United States Patent
Barry (10) Patent No.: US 7,250,027 B2
(45) Date of Patent: Jul. 31, 2007

(54) ARTICULATING VERTEBRAE WITH ASYMMETRICAL AND VARIABLE RADIUS OF CURVATURE

(75) Inventor: James P. Barry, Charlton, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 117 days.

(21) Appl. No.: 10/446,555

(22) Filed: May 28, 2003

(65) Prior Publication Data

US 2004/0044270 A1    Mar. 4, 2004

Related U.S. Application Data

(60) Provisional application No. 60/384,775, filed on May 30, 2002.

(51) Int. Cl.
*A61B 1/00*    (2006.01)

(52) U.S. Cl. .................. 600/141; 600/139; 600/142; 600/146; 604/264; 604/508; 604/523

(58) Field of Classification Search ............... 600/139, 600/141–142, 146
See application file for complete search history.

(56) References Cited

U.S. PATENT DOCUMENTS

| | | | |
|---|---|---|---|
| 5,178,129 A * | 1/1993 | Chikama et al. | 600/142 |
| 5,928,136 A | 7/1999 | Barry | 600/142 |
| 6,610,007 B2 * | 8/2003 | Belson et al. | 600/146 |
| 6,689,049 B1 * | 2/2004 | Miyagi et al. | 600/117 |
| 6,811,532 B2 * | 11/2004 | Ogura et al. | 600/146 |

* cited by examiner

*Primary Examiner*—Linda C. M. Dvorak
*Assistant Examiner*—Matthew J. Kasztejna
(74) *Attorney, Agent, or Firm*—St. Onge Steward Johnston & Reens LLC (57) ABSTRACT

An endoscope has a first segment with a proximal end and a distal end and is symmetric about an axis. A second segment, comprising a flexible and interconnected linkage system, is pivotably coupled to the first segment and, when subject to an applied force, is configurable along an arc having a variable radius of curvature. The linkage system is capable of articulation through an angle from zero degrees through about 280 degrees.

21 Claims, 13 Drawing Sheets

CASE I (CABLE SYMMETRY)

ARTICULATING VERTEBRAE WITH ASYMMETRICAL AND VARIABLE RADIUS OF CURVATURE

PRIOR APPLICATION

Applicant claims priority benefits under 35 U.S.C. §119(e) of U.S. Provisional Patent Application Ser. No. 60/384,775 filed May 30, 2002 which is incorporated herein by reference thereto as if set forth at length.

FIELD OF THE INVENTION

The present invention relates to an endoscope shaft and, more particularly an endoscope shaft made of articulating vertebrae that when subject to a force, are configurable along an arc having a variable radius of curvature.

BACKGROUND OF THE INVENTION

Conventional endoscopes can be articulated in different directions; however, typically these endoscopes cannot be articulated with a variable radius of curvature nor to an angle of more than 180 degrees. Often the endoscope has only a single radius of curvature for the entire articulating length of the shaft. Further, the conventional endoscopes that use articulating vertebrae use a number of vertebrae with identical dimensions connected in series and all oriented the same way.

By limiting the endoscopes to a single radius of curvature, the user of the endoscope is limited as to the regions of the body that are readily accessible by articulation of the endoscope. Because of the limited ability to articulate the endoscope, there is a need for an articulating endoscope capable of being articulated with varying degrees of curvature to permit the operator to locate the endoscope in various locations within the body. Such an endoscope requires a shaft capable of being manipulated with more than one radius of curvature.

SUMMARY OF THE INVENTION

An endoscope has a first segment with a proximal end and a distal end and is symmetric about an axis. A second segment, comprising a flexible and interconnected linkage system, is pivotably coupled to the first segment and, when subject to an applied force, is configurable along an arc having a variable radius of curvature. The linkage system is capable of articulation through an angle from zero degrees through about 280 degrees.

DETAILED DESCRIPTION OF THE INVENTION

Figure 1:
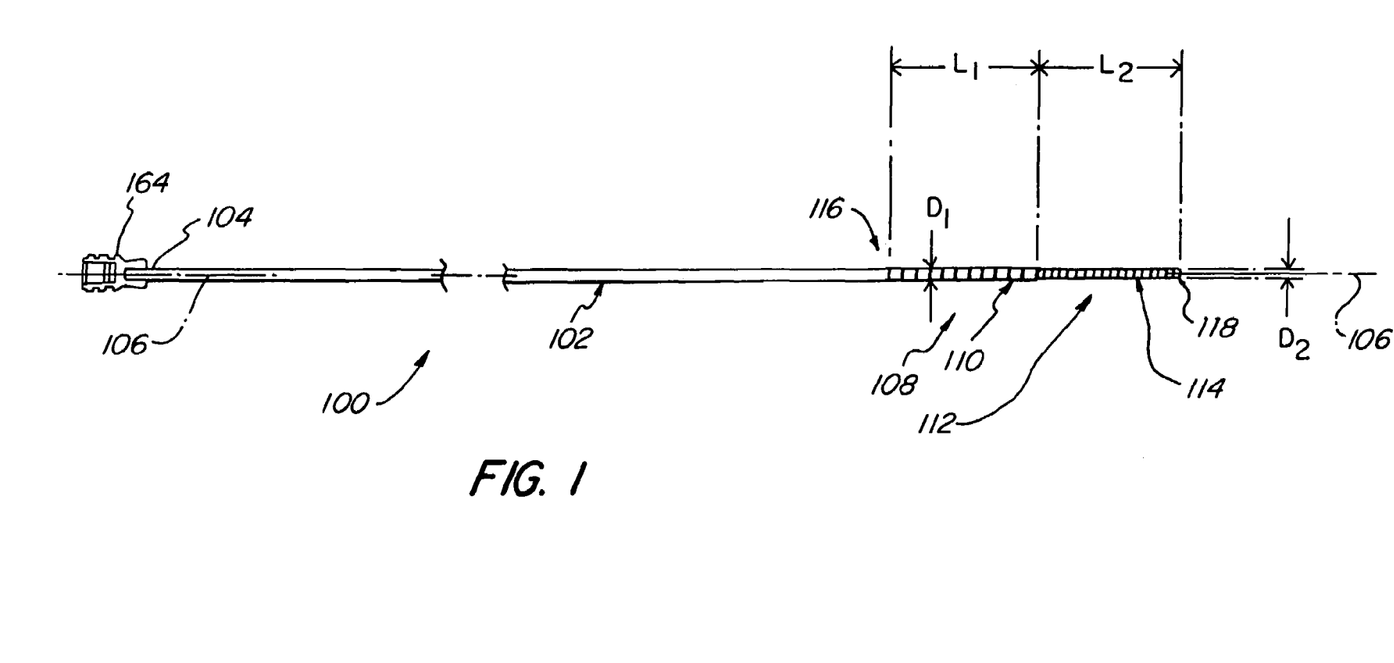
FIG. 1 is a side view of an endoscope shaft with articulating vertebrae.

Referring first to FIG. 1, an articulating endoscope shaft 100 is shown at rest or in an unarticulated configuration along an axis 106. The articulating endoscope shaft 100 has a first insertion shaft segment 102. A second, flexible shaft segment 108 is a linkage system comprising a first set of articulating links or vertebrae 110 attached to and extending over a distance $L_1$ from a distal end 116 of the first insertion shaft segment 102. A third, flexible shaft segment 112 comprising a second set of articulating links or vertebrae 114 is attached to and extends over a distance $L_2$ from the second shaft segment 108. The first insertion shaft segment 102 is connected, at a proximal end 104 thereof, to an endoscope handpiece 164. A distal end 118 of the endoscope 100 and the articulating vertebrae 110, 114 are manipulated by way of the endoscope handpiece 164 through the use of control wires (not shown in FIG. 1) that are threaded through the endoscope 100 and attached to the vertebrae 110, 114.

Figures 2, 3:
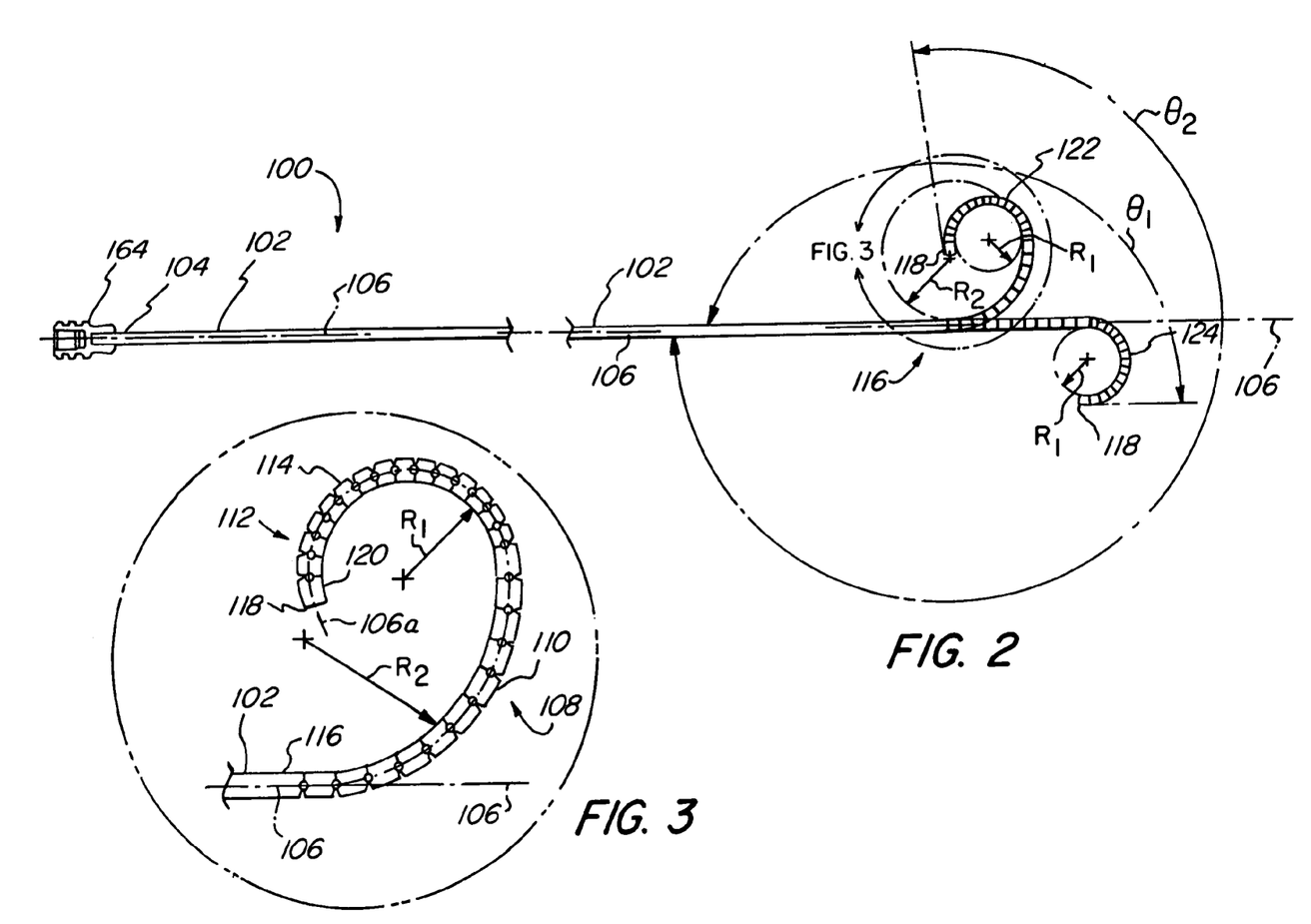
FIG. 2 is a side view of an endoscope shaft in FIG. 1 showing the vertebrae articulated in two different directions.
FIG. 3 is an enlarged view of a segment of the articulated vertebrae shown in FIG. 2.
Figure 4:
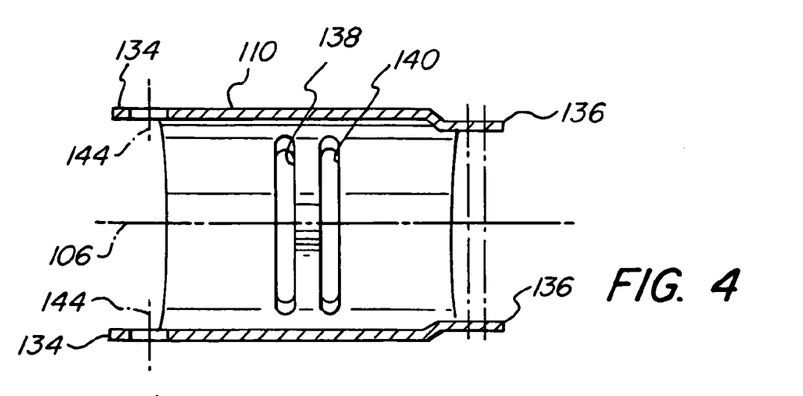
FIG. 4 is a top sectional view of a single vertebra.
Figure 5:
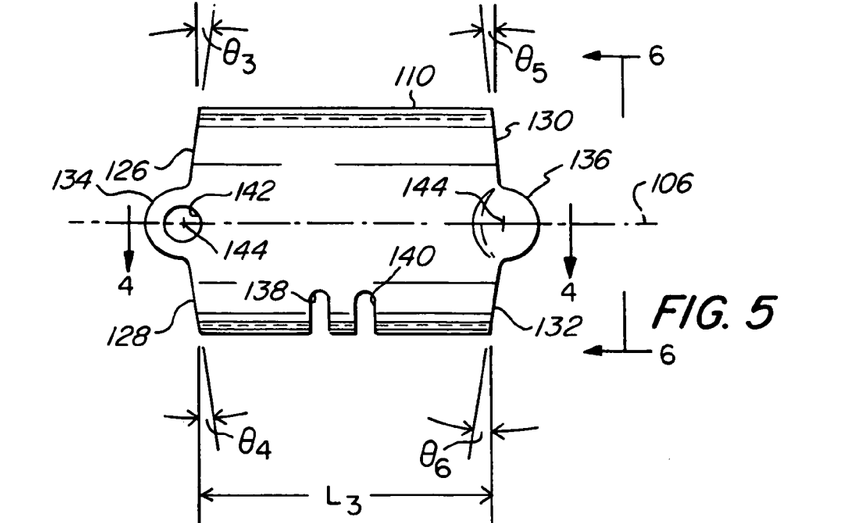
FIG. 5 is a side view of the vertebra shown in FIG. 4.
Figure 6:
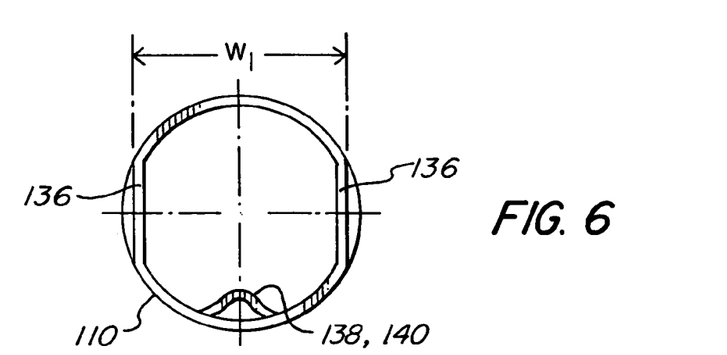
FIG. 6 is an end view of the vertebra shown in FIG. 4.
Figure 7:
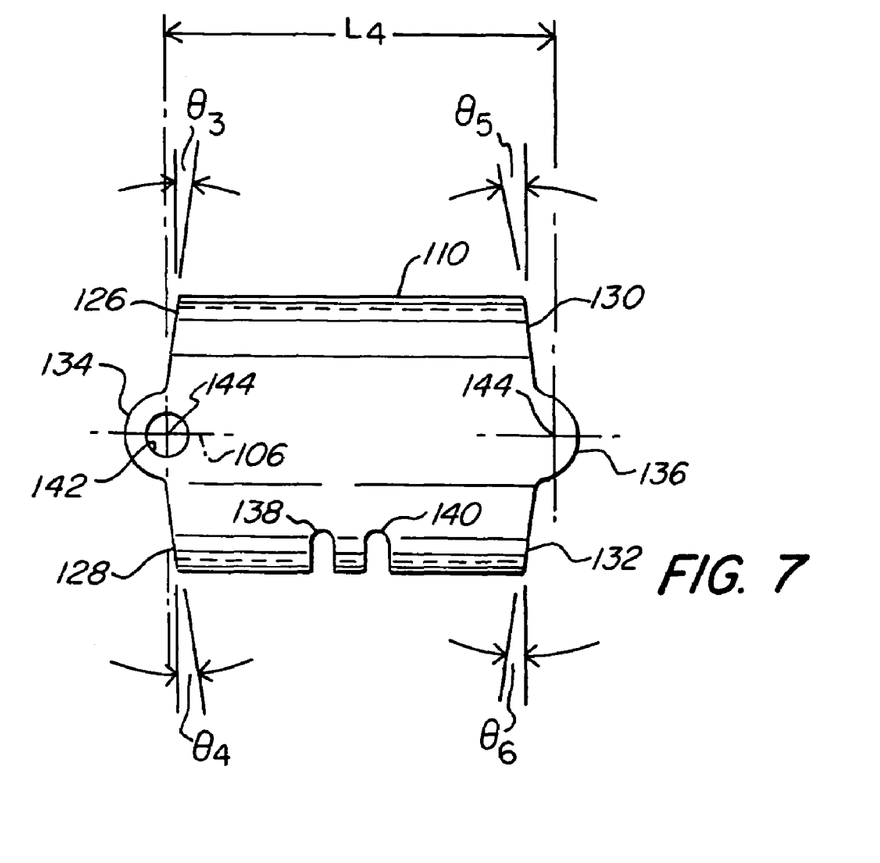
FIG. 7 is another side view of the vertebra shown in FIG. 4.

FIG. 2 shows the endoscope shaft 100 articulated in two different directions or configurations $\theta_1$ and $\theta_2$. Articulated in a first direction $\theta_2$, the vertebrae 110, 114 can be manipulated in such a manner that the vertebrae 110, 114 are displaced from the axis 106 along a first arc 122 wherein the vertebrae 120 (FIG. 3) furthest from the distal end 116 of the first insertion shaft segment 102 is rotated through an angle $\theta_2$ in the range from zero degrees to about 280 degrees. In a similar fashion, when articulated in a second direction $\theta_1$, the endoscope shaft 100 can be manipulated in such a manner that only the vertebrae 114 are displaced form the axis 106 along a second arc 124 wherein the vertebrae 120 furthest from the distal end 116 of the first insertion shaft segment 102 is rotated through an angle $\theta_1$ in the range from zero degrees to about 180 degrees. FIG. 2 shows the endoscope shaft 100 articulated through an angle of $\theta_1$ equal to about 180 degrees, in a direction opposite of the direction shown in FIG. 3, where only the smaller vertebrae 114 are articulated and the articulated endoscope shaft 100 has only one radius of curvature $R_1$.

FIG. 3 shows an enlarged view of the articulating vertebrae segment 108, 112 of the endoscope shaft 100 rotated along an arc 106a having a variable radius of curvature. FIG. 3 shows the endoscope shaft 100 articulated through an angle of about 280 degrees using two different sizes of vertebrae 110, 114. The articulating segment of the endoscope shaft 100 is made up of two segments 108, 112. The first segment 108 uses relatively large diameter ($D_1$) vertebrae 110 with longer lengths $L_3$ or $L_4$ and the second segment 112 uses relatively smaller diameter ($D_2$) vertebrae 114 with smaller lengths $L_5$ or $L_6$. The use of different diameter vertebrae 110, 114 results in the articulating segment of the endoscope shaft 100 capable of having a different angle of manipulation (e.g., $\theta_1$ or $\theta_2$) and a different radius of curvature (e.g., $R_1$ or $R_2$) for different articulating segments of the endoscope shaft 100. FIG. 3 shows the first articulating segment 108 of the endoscope shaft 100 with the larger vertebrae 110 having a larger radius of curvature, $R_2$, than the second articulating segment 112 of the endoscope shaft 100 which has a smaller radius of curvature $R_1$. The larger vertebrae 110 can be seen in detail in FIGS. 4-8, while the smaller vertebrae 114 can be seen in detail in FIGS. 9-13.

Figure 8:
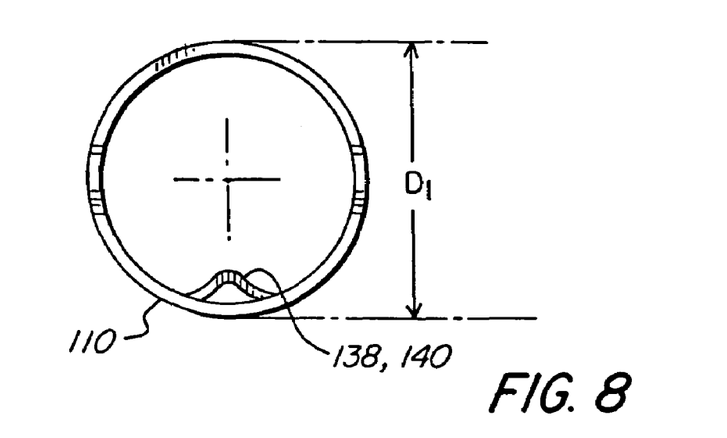
FIG. 8 is a sectional end view of the vertebra shown in FIG. 7.
Figure 9:
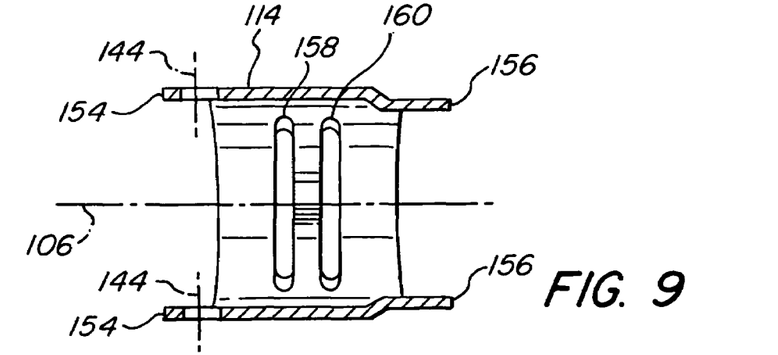
FIG. 9 is a top sectional view of a second vertebra.
Figure 10:
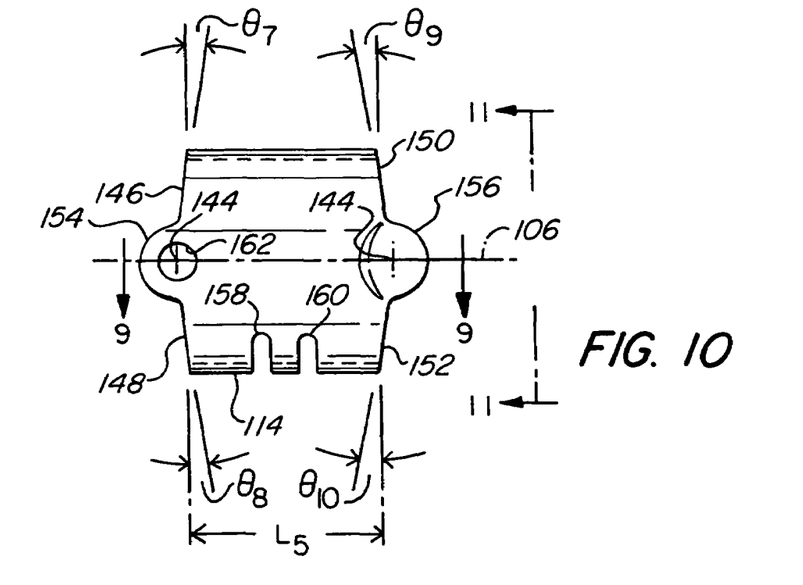
FIG. 10 is a side view of the vertebra shown in FIG. 9.
Figure 11:
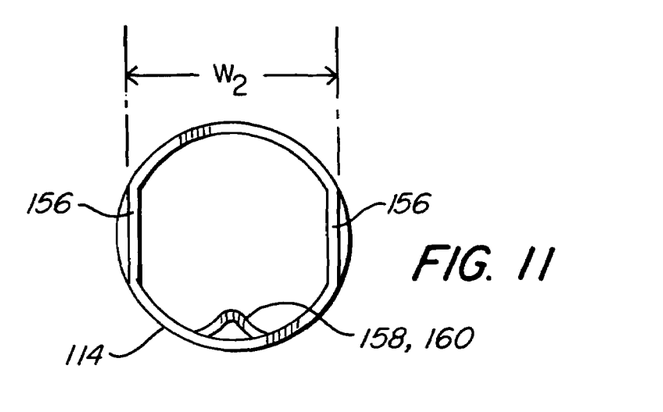
FIG. 11 is an end view of the vertebra shown in FIG. 9.
Figure 12:
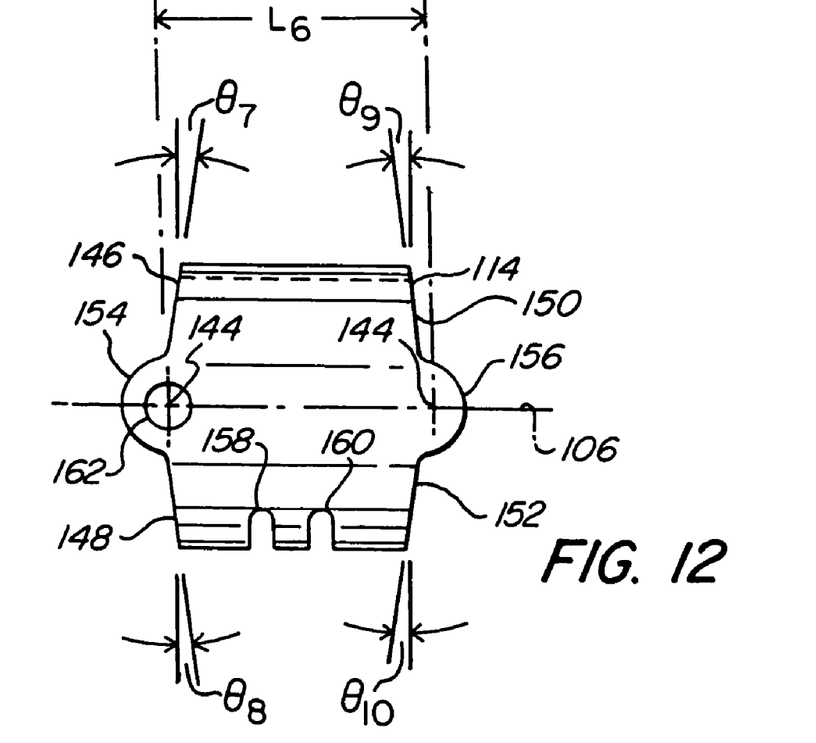
FIG. 12 is another side view of the vertebra shown in FIG. 9.

FIGS. 4-8 show several views of an articulating vertebrae 110. The articulating vertebrae 110 is generally cylindrical in nature and symmetric about the axis 106 with an outside diameter $D_1$ (FIG. 8). The articulating vertebrae 110 includes a front face 126, 128 and a rear face 130, 132. The front face 126, 128 may be beveled at an angle of $\theta_3$ or $\theta_4$ where $\theta_3$ and $\theta_4$ range from zero degrees to about thirty degrees. As best understood from FIG. 5, $\theta_3$ may equal $\theta_4$ or $\theta_3$ may be different from $\theta_4$. Furthermore, the rear face 130, 132 may be beveled at an angle of $\theta_5$ or $\theta_6$ where $\theta_5$ and $\theta_6$ range from zero degrees to about thirty degrees. As best understood from FIG. 5, $\theta_5$ may equal $\theta_6$ or $\theta_5$ may be different from $\theta_6$. Yet further, the articulating vertebrae 110 includes a first pivot member 134 projecting from the front face 126, 128 and a second pivot member 136 projecting from the rear face 130, 132. The front face 126, 128 includes an aperture 142 therein having a rotational axis 144 coincident with the axis 106. As best understood from FIGS. 4 and 5, a pair of the second pivot members 136, of width $W_1$ apart (FIG. 6), on one articulating vertebrae 110, fit securely within a pair of the first pivot members 134 such that any two adjacent and linked pair of articulating vertebrae 110 pivot about a pivot axis 144 to the extent permissible by the front and rear beveled faces 126, 128, 130, 132. The articulating vertebrae 110 is also characterized by either a length, $L_3$ (FIG. 5) or length $L_4$ (FIG. 7) which spans the distance between successive pivot points 144 in the linkage system 108.

Figure 13:
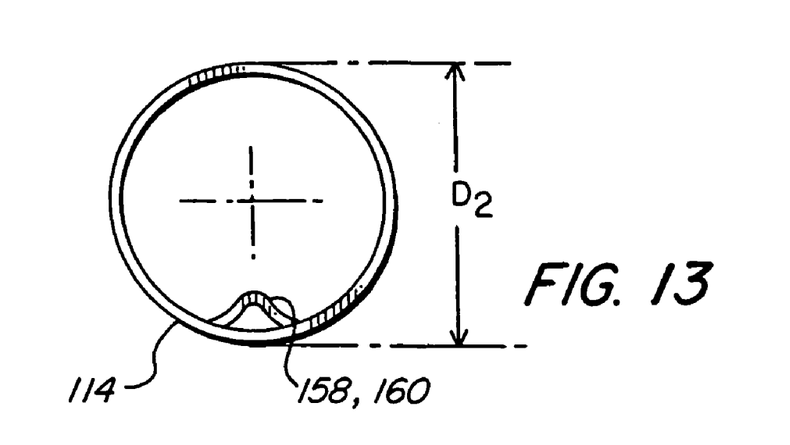
FIG. 13 is a sectional end view of the vertebra shown in FIG. 12.

FIGS. 9-13 show several views of an articulating vertebrae 114. The articulating vertebrae 114 is generally cylindrical in nature and symmetric about the axis 106 with an outside diameter $D_2$ (FIG. 13). The articulating vertebrae 114 includes a front face 146, 148 and a rear face 150, 152. The front face 146, 148 may be beveled at an angle of $\theta_7$ or $\theta_8$ where $\theta_7$ and $\theta_8$ range from zero degrees to about thirty degrees. As best understood from FIG. 10, $\theta_7$ may equal $\theta_8$ or $\theta_7$ may be different from $\theta_8$. Furthermore, the rear face 150, 152 may be beveled at an angle of $\theta_9$ or $\theta_{10}$ where $\theta_9$ and $\theta_{10}$ range from zero degrees to about thirty degrees. As best understood from FIG. 10, $\theta_9$ may equal $\theta_{10}$ or $\theta_9$ may be different from $\theta_{10}$. Yet further, the articulating vertebrae 114 includes a first pivot member 154 projecting from the front face 146, 148 and a second pivot member 156 projecting from the rear face 150, 152. The front face 146, 148 includes an aperture 162 therein having a rotational axis 144 coincident with the axis 106. As best understood from FIGS. 9 and 10, a pair of the second pivot members 156, of width $W_2$ apart (FIG. 11), on one articulating vertebrae 114 fit securely within a pair of the first pivot members 154 such that any two adjacent and linked pair of articulating vertebrae 114 pivot about the pivot axis 144 to the extent permissible by the front and rear beveled faces 146, 148, 150, 152. The articulating vertebrae 114 is also characterized by either a length, $L_5$ (FIG. 10) or length $L_6$ (FIG. 12) which spans the distance between successive pivot points 144 in the linkage system 112.

Figure 14:
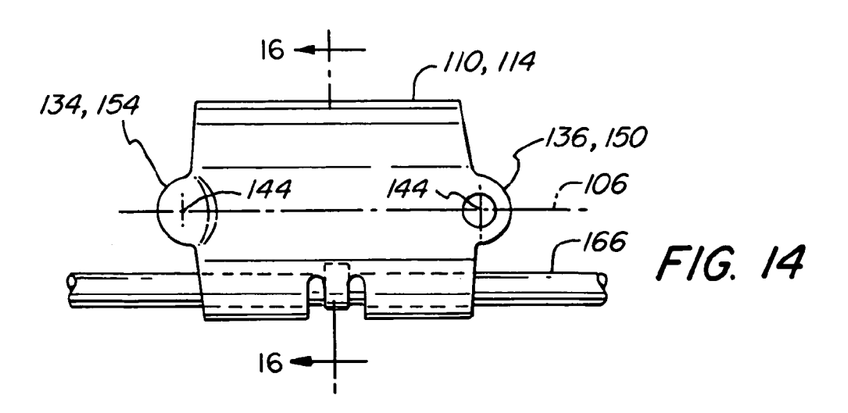
FIG. 14 is a side view of the vertebrae as seen in FIGS. 5, 7, 10 and 12 showing guide wires.
Figure 15:
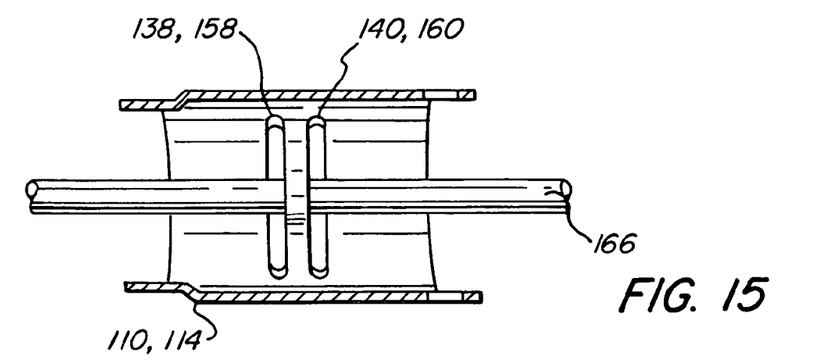
FIG. 15 is a top sectional view of the vertebrae as seen in FIGS. 4 and 9 showing guide wires.

By combining articulated segments 108, 112 having different diameters, bevel angles, lengths and numbers of vertebrae 110, 114, the articulating endoscopic shaft 100 can be manipulated to have two or more radii of curvature (e.g. $R_1$, $R_2$) when articulated in a single direction as seen in FIG. 3, depending upon which articulated segment of the endoscopic shaft 100 is manipulated or actuated. By using vertebrae 110, 114 having different diameters, $D_1$, $D_2$, where $D_1$ is greater than $D_2$, a greater torque, T, (or moment) may be developed in the corresponding vertebrae 110, 114 for $D_1$ than for $D_2$ due to the application of a force by the wire guides 166 (FIGS. 14-16) and as such allowing the vertebrae 110, 114 to be configurable along an arc having a variable radius of curvature. As best understood $D_2$ may be greater than or equal to $D_1$. An explanation of the moments developed in the endoscope will be explained in regard to FIGS. 18-21. Also, the positions of the vertebrae 110, 114 can be arranged in any combination of diameters, bevel angles, lengths, moment arms and numbers of vertebrae 110, 114, along the articulating endoscopic shaft 100 so as to have asymmetrical ranges of manipulation (e.g., $\theta_1 \neq \theta_2$) or variable radii of curvature (e.g., $R_1 \neq R_2$). Such combination of diameters, bevel angles, lengths, moment arms and numbers of vertebrae may be such that the asymmetrical ranges of manipulation or variable radii of curvature are effected depending upon in which direction the endoscopic shaft 100 is manipulated with respect to the axis 106. If the endoscopic shaft 100 is articulated in one direction with respect to the axis 106, it could have a larger angle or range of manipulation and/or radius of curvature, while if it is articulated in the opposite or a different direction with respect to the axis 106, it could have a smaller angle or range of manipulation and/or smaller radius of curvature. Furthermore, the same segment of the articulating endoscopic shaft 100 could have a different radius of curvature or angle of manipulation, depending upon the direction the shaft is articulated.

The arrangement of the vertebrae 110, 114 can also permit the endoscopic shaft 100 to be bent or manipulated in a single direction with respect to the axis 106 with different radii of curvature for different segments of the shaft 100. By adjusting the lengths, $L_3$, $L_4$, of different vertebrae 110, 114 or the number of each vertebrae 110, 114 used in each section 108, 112 of the articulating segment of the shaft 100, the endoscopic shaft 100 can be designed to have any number of combinations of radii curvatures for manipulation. For example, the endoscopic shaft 100 can be designed to have an increasing or decreasing radius of curvature as articulation of the articulated segments 108, 112 increases or decreases. The vertebrae 110, 114 and endoscopic shaft 100 can be specifically designed with the various radii of curvature needed to access specific areas within a body. By adjusting the number, length, diameter and bevel angle of the face of the vertebrae 110, 114, one can affect the bending properties of the articulated endoscopic shaft 100, such as symmetry with respect to the axis 106, the angle of articulation (e.g., $\theta_1$, $\theta_2$) and radius of curvature (e.g., $R_1$, $R_2$).

The vertebrae 110, 114 can be joined in any number of ways. FIG. 3 shows a series of large diameter vertebrae 110 pivotably connected to a series of smaller diameter vertebrae 114. The larger diameter vertebrae 110 are pivotally connected in series by mating and connecting the pivot members which extend from each end of each vertebrae 110, 114. The smaller diameter links 114 are pivotally connected in a similar manner. The ends of each of the vertebrae 110, 114 has a beveled surface which makes contact with the end surface of each adjacent vertebrae 110, 114 when the endoscopic shaft 100 is articulated. The larger the bevel angle, the greater the potential angle of articulation of the shaft because, as each vertebrae 110, 114 is actuated, it will continue to move in a particular direction until it comes in contact with its adjacent vertebrae and can no longer be actuated. By using vertebrae of different length and different bevel angles, one can control the bending properties of the endoscopic shaft 100.

Figure 16:
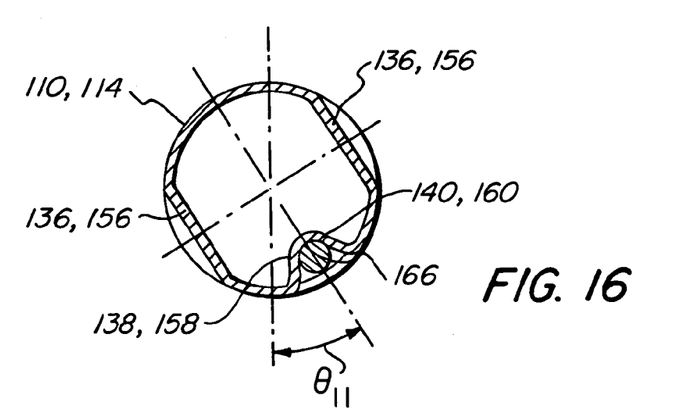
FIG. 16 is a sectional view of the vertebrae of FIG. 14.
Figure 17:
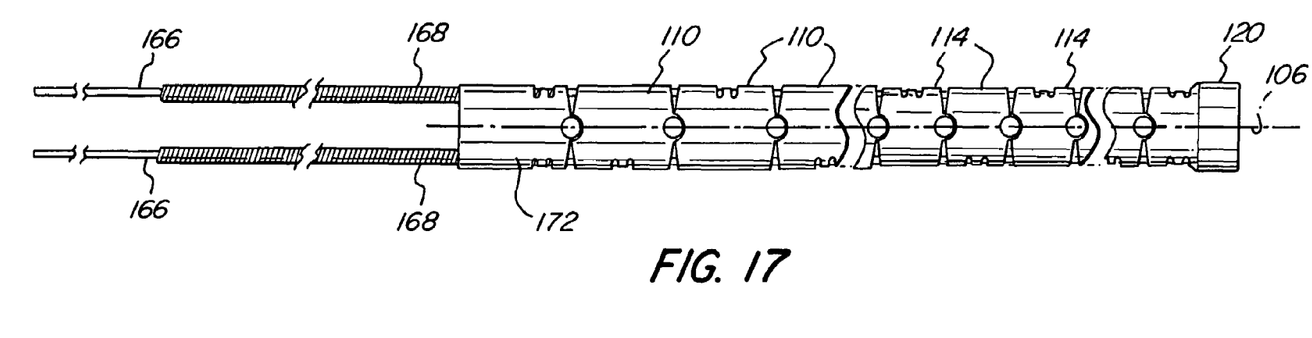
FIG. 17 is a side view of an endoscope shaft with articulating vertebrae showing guide wires.

Each vertebrae 110, 114 has two openings or slots 138, 140, 158, 160 in its side that define means for guiding the guide wires 166 that are manipulated to articulate the first and second segments 108, 112 of the shaft 100. The vertebrae 110, 114 can be oriented in a variety of ways with respect to the openings 138, 140, 158, 160 in their sides. For example, the vertebrae 110, 114 could be assembled in a manner where the orientation of the openings 138, 140, 158, 160 for each consecutive vertebrae 110, 114, is rotated through an angle $\theta_{11}$ with respect to an adjacent vertebrae (e.g. 180 degrees). As such, a first guide wire 166 passing through the inside of the vertebrae 110, on one side of the endoscopic shaft 100, would therefore be attached to every other vertebrae 110 that had its openings 138, 140 oriented on the same side of the endoscopic shaft 100. A second guide wire 166 passing through the opposite side of the endoscopic shaft 100 would be attached to all the other vertebrae 114 that were oriented to have their openings 158, 160 on the opposite side of the endoscopic shaft 100. As seen in FIG. 17, the guide wires 166 are woven through the side openings 138, 140, 158, 160 in each or every other vertebrae 110, 114. The guide wires 166 are attached only to the end vertebrae 120. FIG. 16 shows that the guide wires 166 may be offset at an angle of $\theta_{11}$. It will also be understood that the angle $\theta_{11}$ may vary from one vertebrae to the next.

Figure 18:
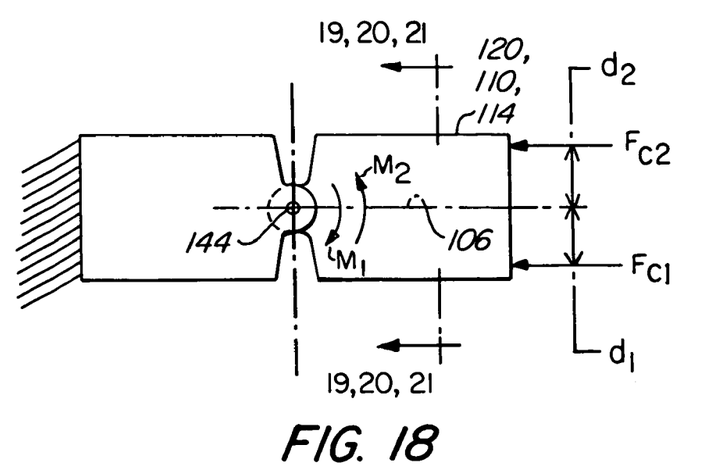
FIG. 18 is a side view of a segment of an endoscope shaft with articulating vertebrae showing moments developed therein due to forces applied to guide wires.
Figure 19:
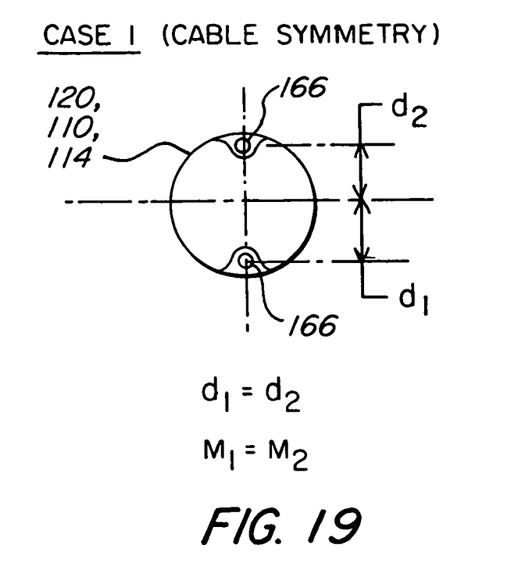
FIG. 19 is a sectional view of the segment of the endoscope of FIG. 18 showing guide wire symmetry.
Figure 20:
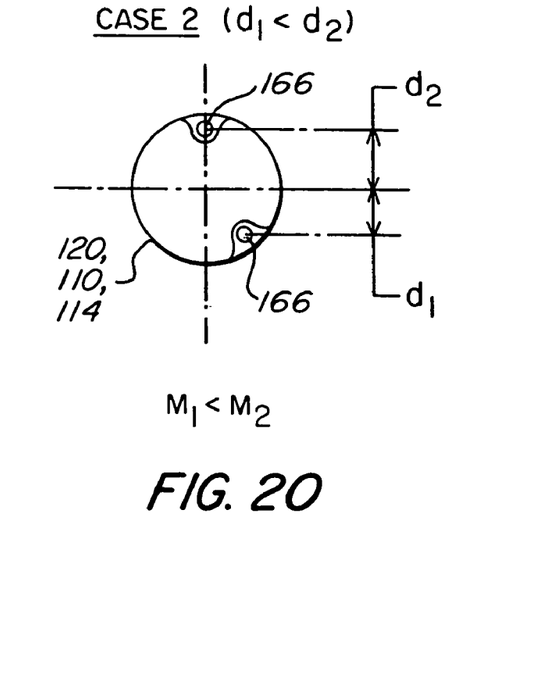
FIG. 20 is a sectional view of the segment of the endoscope of FIG. 18 showing asymmetrical guide wires.
Figure 21:
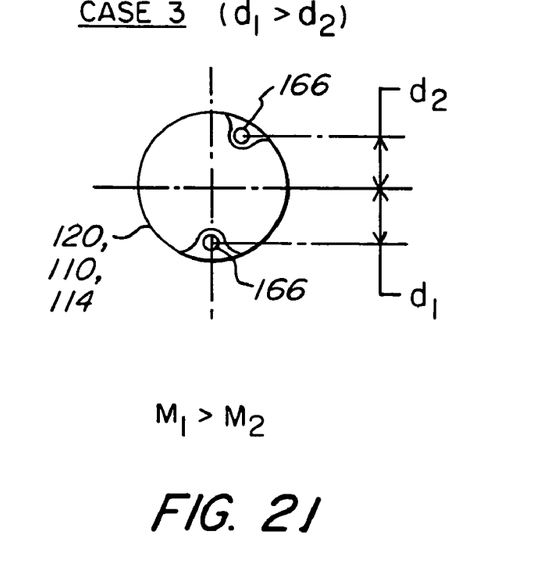
FIG. 21 is a sectional view of the segment of the endoscope of FIG. 18 showing asymmetrical guide wires.

FIG. 18 depicts a side view of a segment of the endoscope shaft 100 with articulating vertebrae 110, 114, showing moments, $M_1$, $M_2$ developed about the rotational axis 144 due to forces $F_{c1}$ and $F_{c2}$ applied to guide wires 166. The forces are applied at distances $d_1$ and $d_2$ (moment arms) from the axis 106 and the moment $M_i = F_{ci} \times d_i$, i=1,2. Three conditions are possible in the arrangement of the guide wires 166 whereby different moments are developed. FIG. 19 depicts a sectional view of the segment of the endoscope shaft of FIG. 18 showing guide wire symmetry whereby $d_1 = d_2$ and $M_1 = M_2$ for equal forces $F_{c1}$ and $F_{c2}$. FIG. 20 depicts a sectional view of the segment of the endoscope shaft of FIG. 18 showing asymmetrical guide wires whereby $d_1 < d_2$ and $M_1 < M_2$ for equal forces $F_{c1}$ and $F_{c2}$. FIG. 21 depicts a sectional view of the segment of the endoscope shaft of FIG. 18 showing asymmetrical guide wires whereby $d_1 > d_2$ and $M_1 > M_2$ for equal forces $F_{c1}$ and $F_{c2}$. The asymmetrical guide wire conditions of FIGS. 20 and 21 may also be effected as in FIG. 19 by adjusting $d_1$ and $d_2$ therein. The asymmetrical guide wire condition allows the endoscope shaft 100 to be articulated through an angle $\theta_2$ of from zero degrees through about 280 degrees.

Figure 22:
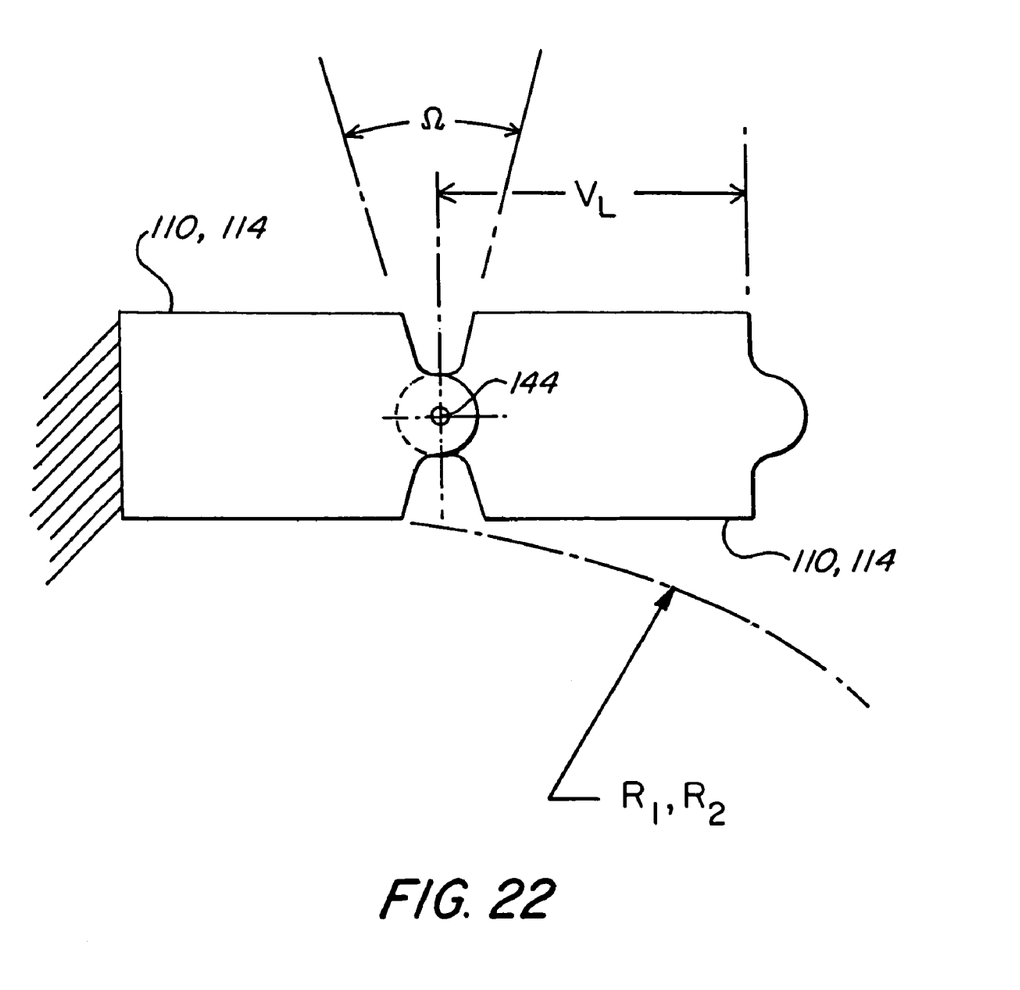
FIG. 22 is a side view of a segment of an endoscope shaft with articulating vertebrae showing dimensions by which the radius of curvature of the endoscope is calculated.

FIG. 22 is a side view of a segment of an endoscope shaft with articulating vertebrae 110, 114 showing the dimensions $V_L$, $\Omega$, by which the radius of curvature, $R_1$, $R_2$, of the endoscope can be calculated. The radii of curvature, $R_1$, $R_2$ can be calculated from the Equation (1):

$$R_i = \frac{V_L}{2\sin\left(\frac{\sum \Omega}{2 \sum V}\right)} \quad (1)$$

where i=1, 2. In Eq. 1 $V_L$ is the length of the vertebrae, $\Omega$ is the bend angle between adjacent vertebrae, $\Sigma\Omega$ is the total bend angle, $\Sigma V$ is the total number of vertebrae links.

Figure 23:
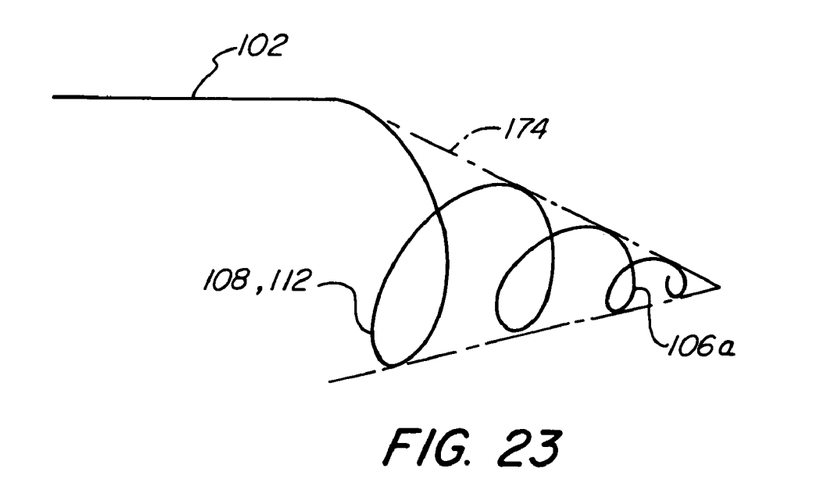
FIG. 23 is a first view showing a configuration of the vertebrae of FIG. 3 articulated along an arc of decreasing radius on the surface of a cone.
Figure 24:
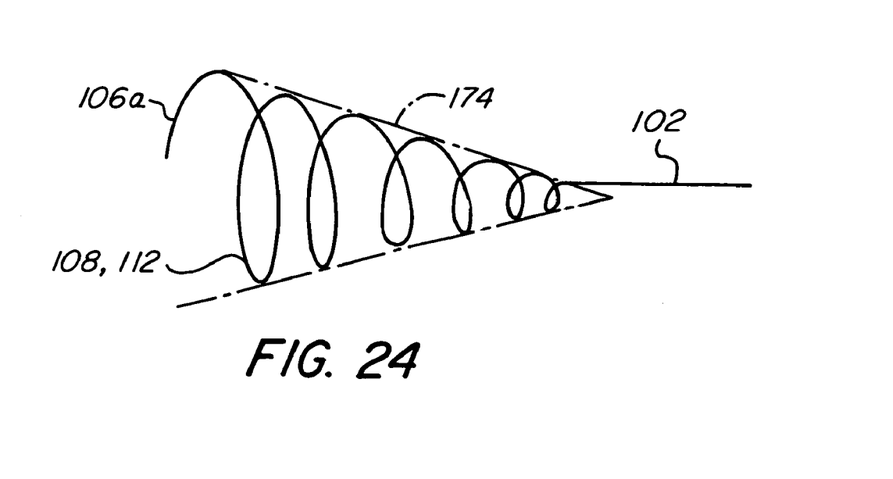
FIG. 24 is a second view showing a configuration of the vertebrae of FIG. 3 articulated along an arc of increasing radius on the surface of a cone.
Figure 25:
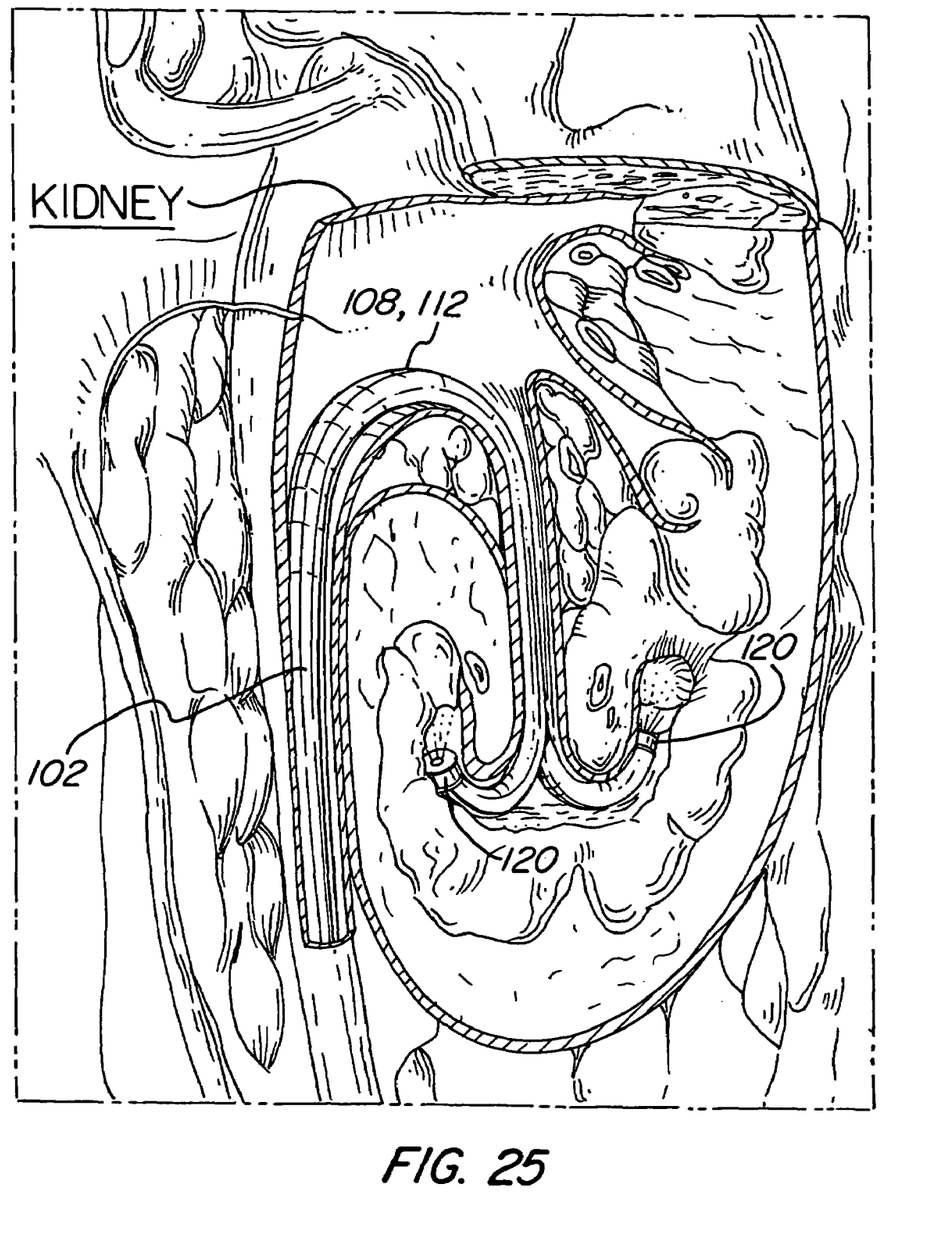
FIG. 25 is a view of the endoscope of FIG. 3 accessing remote and out of the way regions of a kidney.

As seen in FIGS. 23 and 24 and as best understood from FIGS. 2, 3, 16 and 19-21, due to the angular location of the guide wires 166 about the axis 106, or the angular rotation of a front face of a vertebrae with respect to a rear face thereof (i.e. the value of $\theta_{11}$), and the varying moments developed in the first and second segments 108, 112 of the endoscope, the arc 106a along which the first and second segments 108, 112 are configured may lie either within a plane or on the surface of a geometrical body such as a cone 174 such that the arc 106a is extraplanar in nature. Such out of plane configuration, as well as an angle of articulation of greater than 180 degrees, of the endoscope 100 allows, for example, a surgeon much greater flexibility in viewing or accessing previously inaccessible locations or irregularly shaped parts or cavities of a body such as the kidneys (FIG. 25).

Thus it is seen that based upon the forgoing description of the invention a flexible endoscope is disclosed comprising a first segment having a proximal end and a distal end thereof. The first segment is symmetric about an axis. A second segment comprising a flexible and interconnected linkage system is pivotably coupled to the first segment and, when subject to a force, is configurable along an arc having a variable radius of curvature.

It should be understood that any reference to first, second, front, rear, etc. or any other phrase indicating the relative position of one element or device with respect to another is for the purposes of explanation of the invention and, unless other wise noted, is not to be construed as limiting the invention. Furthermore, while preferred embodiments have been shown and described, various modifications may be made thereto without departing from the true spirit and scope of the invention. Accordingly, it is to be understood that the present invention has been described by way of illustration and not limitation.

What is claimed is:

1. An endoscope comprising:
   a first segment having a proximal end and a distal end thereof wherein the first segment is symmetric about an axis of the segment body; and
   a second segment comprising
      a first set of interconnected links having a first length, pivotably coupled to the first segment and bendable away from the axis; and a second set of interconnected links having a second length that is different from the first length and connected to the first set of links and bendable away from the axis in the same radial direction as the first set of links to a smaller radius of curvature than the first set of links, the second set of links having at least one angle of articulation different than the first set of links;

a set of guide wires for applying a force to the first and second set of links, the guide wires circumferentially positioned at varying rotational angles about the axis for each individual link; and wire guides for guiding the set of guide wires along the first and second set of links, said wire guides circumferentially positioned at varying rotational angle about the axis for each individual link, the varying rotational angle being variable for each individual link.

2. The endoscope according to claim 1 wherein each individual link of the first set of links comprises:
a front face beveled at a first and second angle;
a rear face beveled at a third and fourth angle;
a first pivot member projecting from the front face; and
a second pivot member projecting from the rear face;
wherein the first pivot member of one link is pivotably coupled about a rotational axis to the second pivot member of a second link.

3. The endoscope according to claim 1 wherein the front face of each of the pivotable links is rotated by an angle of θ about the axis with respect to the rear face wherein the arc is extraplanar.

4. The endoscope according to claim 1 wherein the set of guide wires are attached to the individual links at variable distances from the axis.

5. The endoscope according to claim 1 wherein the first and second sets of links, when bent away from the axis, form an arc that subtends an angle of from zero degrees to greater than 180 degrees.

6. The endoscope according to claim 5 wherein the radius of curvature increases along the arc.

7. The endoscope according to claim 5 wherein the radius of curvature decreases along the arc.

8. The endoscope according to claim 5 wherein the arc lies in a plane.

9. The endoscope according to claim 8 wherein the arc is a spiral.

10. The endoscope according to claim 9 wherein the spiral has an increasing radius of curvature.

11. The endoscope according to claim 9 wherein the spiral has a decreasing radius of curvature.

12. The endoscope according to claim 5 wherein the arc lies on a geometrical body.

13. The endoscope according to claim 12 wherein the geometrical body is a cone.

14. The endoscope according to claim 1 wherein each radius of curvature for each set of links is calculated according to the following equation:

$$R_i = \frac{V_L}{2\sin\left(\frac{\Sigma\Omega}{2\Sigma V}\right)}$$

wherein i=1, 2, $V_L$ is the length of the link, $\Omega$ is the bend angle between adjacent links, $\Sigma\Omega$ is the total bend angle, $\Sigma V$ is the total number of links.

15. A flexible endoscope comprising:
pivotably interconnected first set of links, each link having a first lenath and second set of links, each link having a second length that is different from the first length, the second set of links is bendable to a radius of curvature smaller than the radius of curvature to which the first set of links is bendable in the same radial direction thereas;

a plurality of guide wires connected to the first and second sets of links for applying force thereto such that the first and second sets are subject to different torques, the plurality of guide wires are circumferentially positioned at varying rotational angles about an axis for each individual link; and wire guides for guiding the set of guide wires along the endoscope, said wire guides circumferentially positioned at varying rotational angle about the axis for each individual link, the varying rotational angle being variable for each individual link.

16. The endoscope according to claim 15 wherein the first and second sets of links, when bent away from the axis, form an arc that subtends an angle of from zero degrees to greater than 180 degrees.

17. The endoscope according to claim 16 wherein the arc is a spiral.

18. The endoscope according to claim 17 wherein the spiral has an increasing radius of curvature.

19. The endoscope according to claim 17 wherein the spiral has a decreasing radius of curvature.

20. The endoscope according to claim 16 wherein the arc lies on a geometrical body.

21. The endoscope according to claim 20 wherein the geometrical body is a cone.

* * * * *